(12) United States Patent
Reime

(10) Patent No.: US 9,995,839 B2
(45) Date of Patent: Jun. 12, 2018

(54) METHOD FOR DETERMINING AT LEAST ONE PHYSICAL PARAMETER USING A SENSOR UNIT

(71) Applicant: Gerd Reime, Bühl (DE)

(72) Inventor: Gerd Reime, Bühl (DE)

( * ) Notice: Subject to any disclaimer, the term of this patent is extended or adjusted under 35 U.S.C. 154(b) by 17 days.

(21) Appl. No.: 15/311,937

(22) PCT Filed: May 22, 2015

(86) PCT No.: PCT/EP2015/061373
§ 371 (c)(1),
(2) Date: Nov. 17, 2016

(87) PCT Pub. No.: WO2015/177337
PCT Pub. Date: Nov. 26, 2015

(65) Prior Publication Data
US 2017/0097438 A1 Apr. 6, 2017

(30) Foreign Application Priority Data

May 23, 2014 (DE) .......... 10 2014 007 491
Jul. 22, 2014 (DE) .......... 10 2014 010 671

(51) Int. Cl.
*G01R 27/28* (2006.01)
*G01V 3/10* (2006.01)
(Continued)

(52) U.S. Cl.
CPC ............. *G01V 3/10* (2013.01); *G01N 27/028* (2013.01); *G01R 27/00* (2013.01); *G01R 27/26* (2013.01);
(Continued)

(58) Field of Classification Search
CPC .. G01R 27/2611; G01R 27/26; G01R 27/267; G01R 27/00; G01L 21/30; G01N 27/62; G01N 27/64; H01J 41/00; H01J 41/02
(Continued)

(56) References Cited

U.S. PATENT DOCUMENTS 4,030,026 A   6/1977 Payne
4,724,709 A   2/1988 Antonazzi
(Continued)

FOREIGN PATENT DOCUMENTS

DE   102012001202 A1   2/2013
DE   102012019329 A1   4/2014
(Continued)

OTHER PUBLICATIONS

International Search Report for corresponding application PCT/EP2015/061373 filed May 22, 2015; dated Jul. 15, 2015.

*Primary Examiner* — Jermele M Hollington
*Assistant Examiner* — Raul Rios Russo
(74) *Attorney, Agent, or Firm* — Cantor Colburn LLP

(57) ABSTRACT

In a method for determining at least one physical parameter, a sensor unit which is activated by at least one periodic excitation (1.4) is provided, wherein the sensor unit has at least one detection region in which changes of the parameter in the surroundings of the sensor unit lead to output signal (1.7) from the sensor unit. The sensor unit is wired such that if there are no changes of the parameter in the detection region the output signal (1.7) is a zero signal or virtually a zero signal at the output of the sensor unit, whereas if there are changes of the parameter in the detection region the output signal (1.7) is a signal that is not zero and has a specific amplitude and phase. In a closed control loop, the non-zero signal in the receive path is adjusted to zero using a control signal to achieve an adjusted state even in the (Continued)

presence of changes of the parameter in the detection region. The control signal is evaluated in order to determine the physical parameter. The output signal (1.7) from the sensor unit is reduced substantially to the fundamental wave of the excitation (1.4) and the output signal (1.7) is controlled to zero in the entire phase space by means of at least one pulse width modulation. A temperature-stable, fully digital measuring system is provided as a result of the fact that the at least one pulse width modulation itself generates a correction signal with a variable pulse width and possibly a variable phase which is then added to the output signal (1.7) from the sensor unit and the output signal is thereby controlled to zero in the entire phase space, wherein the pulse width of the correction signal and/or the phase of the correction signal is/are determined by the deviations of the output signal (1.7) from zero.

15 Claims, 6 Drawing Sheets

(51) Int. Cl.
| | | |
|---|---|---|
| *G01R 27/26* | (2006.01) | |
| *G01R 27/00* | (2006.01) | |
| *G01N 27/02* | (2006.01) | |
| *G01N 27/62* | (2006.01) | |
| *H01J 41/02* | (2006.01) | |
| *H01J 41/00* | (2006.01) | |
| *G01N 27/64* | (2006.01) | |

(52) U.S. Cl.
CPC ........ *G01R 27/267* (2013.01); *G01R 27/2611* (2013.01); *G01N 27/62* (2013.01); *G01N 27/64* (2013.01); *H01J 41/00* (2013.01); *H01J 41/02* (2013.01)

(58) Field of Classification Search
USPC ... 324/76.11–76.83, 459, 600, 649, 654, 655
See application file for complete search history.

(56) References Cited

U.S. PATENT DOCUMENTS

| 5,729,143 A | 3/1998 | Tavernetti | |
|---|---|---|---|
| 2003/0038623 A1* | 2/2003 | Draxelmayr | G01D 5/24452 324/166 |
| 2005/0030010 A1* | 2/2005 | Jones | D06F 39/003 324/207.24 |
| 2007/0286294 A1* | 12/2007 | Spahlinger | G01C 19/56 375/242 |

FOREIGN PATENT DOCUMENTS

| DE | 102013226887 A1 | 6/2015 |
|---|---|---|
| EP | 1059542 A2 | 12/2000 |
| WO | 2012104086 A2 | 8/2012 |

\* cited by examiner

METHOD FOR DETERMINING AT LEAST ONE PHYSICAL PARAMETER USING A SENSOR UNIT

CROSS REFERENCE TO RELATED APPLICATIONS

The present disclosure relates to and claims the priority of German patent application 10 2014 007 491.9, filed on 23 May 2014, and German patent application 10 2014 010 671.3, filed on 22 Jul. 2014, the disclosure of which is hereby expressly incorporated by reference into the subject matter of the present application in its entirety.

TECHNICAL FIELD

The disclosure relates to a method for determining at least one physical parameter by means of a sensor unit.

BACKGROUND

The most diverse methods for determining at least one physical parameter by means of a sensor unit are known from the prior art. These measurement methods frequently have in common a dependence on temperature, which is explained below with reference to inductive measuring systems, even though these statements may also apply to any other principles of measurement as desired, such as in particular capacitive or resistive measuring systems, or indeed optical or chemical measuring systems, provided the physical measured value is converted to an electrical value.

Inductive methods for detecting an object having an inductive effect have long been known. Examples of products extend from industrial proximity sensors, to position encoders, right through to treasure detecting devices. These sensors are typically provided with a coil system in which an electromagnetic field is periodically emitted and the influence on the field by the object having an inductive effect (target) is measured.

Preferably, inductive systems are used in which the transmitting coil and the receiving coil are magnetically uncoupled. In the absence of the target, the emitted magnetic field has no effect in the receiving coil. A metal object close to the transmitting field changes the magnetic lines of force or the induced eddy currents. As the eddy currents decay, a field is generated in the object and can in turn be received by the receiving coil. The received currents are naturally very small and have to be amplified for further evaluation. Depending on the form taken by the sensor system, this amplification may be more than a factor of 1 000. A problem that occurs here in practice is the effect of temperature on the analogue chips in the receive path.

The prior art, such as DE-A 10 2012 019 329, thus also discloses systems in which the received signal is controlled to give zero even when there is an influence from metal. For this purpose, for example the received signal produced in a receiving coil is controlled to give substantially zero by a compensation value that is generated in analogue manner, for example in the form of a periodically triggered voltage. The output signal of the sensor unit is reduced substantially to the fundamental wave of the excitation and if necessary the output signal is controlled to give zero in the entire phase space by means of a pulse width modulation. However, the output signal is not evaluated but rather the control signal in order to determine therefrom changes in the detection region, for example the approach of an object. The analogue signals used, by means of which the received signal of the coil system is entirely or partly compensated to zero, are not an optimum point. Generating signals that are controlled in analogue manner requires semiconductor components which are themselves relatively temperature-critical, with the result that a great deal of complexity is needed for precise measurement that is independent of temperature.

German patent application DE 10 2013 226 887, which is older but published later, discloses the fact the signal determined in the receive path at the same time contains information on the shape and/or composition of the target or the size of the surface area of the target in the detection region of the coil system. Here, the movement or position of the target are determinable by the change in shape and/or the change in composition, independently of the distance from the target to the coil system. If this information is processed by vector analysis, the desired further information can consequently be deduced in a differentiated manner. For this purpose, continuous control takes place in a closed-loop control circuit, such that the received signal is always controlled to give a zero value. Thus, a target in the detection region of the transmitting/receiving coil system always results in a change in the control signals. Thus, a deviation from the compensated condition, as an item of information relating to the target, is inherent in the control signal. If a target that has a shape or composition that is variable in a direction of measurement is used, and if, once the control variables have been appropriately taken into account, the deviation thereof from a compensated output condition is applied to a four-quadrant presentation, it can be established that the angle that an imaginary vector makes with the horizontal axis of the coordinate system is a measure of the movement of the target in the direction of measurement, while the magnitude of the imaginary vector is a measure of the distance of the target normal to the direction of measurement. Thus, the position of the target in the direction of measurement can be inferred separately from the distance of the target normal to the direction of measurement, or, depending on the target, the composition and the shape of the target can be inferred.

U.S. Pat. No. 5,729,143 A discloses an inductive metal detector in which, in a calibration phase and using a pulse width and phase modulation, undesired received signals are canceled out. Using the adjustment that is performed in this way, measurement is then performed continuously, wherein the output signals of the receiving coil for measurement are evaluated. A comparable procedure is also performed in the case of a metal detector according to U.S. Pat. No. 4,030,026 A in order to exclude mineral soils or other background conditions from the measurements.

BRIEF SUMMARY

Taking this prior art as a starting point, the disclosure provides a temperature-stable, fully digital measuring system.

This is achieved by a method for determining at least one physical parameter by means of a sensor unit.

The disclosure results from the following considerations, which are explained below by the example of an inductive proximity sensor, even though the method can also be used for any other principles of measurement as desired, such as in particular capacitive or resistive measuring systems, or indeed optical and chemical measuring systems, provided the physical measured value is converted to an electrical value.

Typically, electrical values delivered by a sensor of this kind are very small, so that an amplification or corresponding signal processing is performed before these signals can be evaluated. Although today's A/D converters in microprocessors are already very sensitive in order to convert an analogue signal into a digital signal, in some sensors the occurring changes in value are so small, yet still have to be detected, that it is beyond the capability even of an A/D converter of this kind. The disclosure takes as its starting point the fact that it is possible to compensate such a small signal by a signal that is just as small but entirely digitally generated, to give a zero value. This "zero signal" can then be amplified to any desired level and supplied to the A/D converter of the microprocessor. If this zero signal is kept constantly at zero by a closed-loop control, temperature-related influences and changes in amplification in the system that are caused thereby no longer have any influence on the control value. It is also advantageous that purely digital signals of pulse width modulation (PWM) only need be divided down to a very small value passively, for example by means of resistors, in order to compensate digitally the signal at the location at which it is produced, in this case the receiving coil, in the entire phase space. Digital signals are typically not temperature-critical, since they only consist of zeros and ones.

For the exemplary case of an inductive sensor, a purely digital signal that comprises a plurality of PWM segments is added to the signal of the receiving coil directly at the location at which it is produced. Here, although a harmonic wave spectrum occurs, this can be suppressed by separating the harmonic content of the received signal from the fundamental wave. In the simplest case, this is done by setting up a resonance on the fundamental wave in the receiving coil system.

The pulse width modulation can be varied digitally in discrete steps and is not subject to any effect of temperature (in general, clock frequencies are generated by quartz, which here can be assumed to be stable). Depending on the pulse width, this periodically supplies a variable energy content to the signal in the receive path. In order to achieve optimum cancelation of the output signal of the receiving coil, either the energy must be supplied in a manner varying in quantity (length of the PWM) and varying in respect of the correct point in time per phase, or the energy must be supplied in phase at two fixed points in time that are separated from one another, e.g. at 0° and 180° and at 90° and 270°, in each case inverted in respect of one another. In all cases, only a signal that is generated purely digitally is required to control an output signal of the receiving coil continuously to give it zero value. All the subsequent amplifier stages serve only to decide whether the receiving coil is not equal to zero, and can thus also be regarded as a digital system.

In practice, the amplification used can be so high that only the amplifier noise still applies across the output of the amplifier in the receive path, and, as the evaluation basis for the pulse width modulation, this noise is digitally evaluated only statistically for high and low incidence. In contrast to analogue temperature-dependent measurement, in which the measured signal is dependent on amplitude, with this measurement principle the measured value is obtained from the unambiguous, temperature-independent item of digital information. This item of digital information is further processed digitally and the control variable for the pulse width modulation is calculated from these values.

Current methods of control engineering, such as PID control algorithms, may also be applied here in the digital signal processing.

The values of the digital correction signal that are obtained in this way thus entirely represent the inductive influences of the target on the transmitting/receiving coil system.

Preferably, when a relatively high excitation frequency of, for example, 400 kHz is used by way of a combination of a plurality of, for example four, pulse width modulations, a tri-state correction signal is produced that controls the inductive effect of the target to give zero, for example at four points in the phase space. These four points are each offset by 90° to one another in the phase space. It is also possible to select more points if operation is with a low frequency, for example smaller than 10 kHz, since in that case the processor has sufficient processing time to calculate a plurality of points in the phase space.

Further advantages are apparent from the subclaims and the description given below of preferred exemplary embodiments.

BRIEF DESCRIPTION OF THE FIGURES

The disclosure is explained in more detail below with reference to exemplary embodiments illustrated in the attached Figures. In the Figures.

DETAILED DESCRIPTION

The disclosure is now explained in more detail by way of example, with reference to the attached drawings. However, the exemplary embodiments are only examples, which are not intended to restrict the inventive concept to a particular arrangement. Before the disclosure is described in detail it should be pointed out that it is not restricted to the respective constituent parts of the device and the respective method steps, since these constituent parts and method may vary. The terms used here are merely intended to describe particular embodiments and are not used restrictively. Moreover, where the singular or the indefinite article is used in the description or the claims, this also refers to a plurality of these elements unless the overall context unambiguously indicates otherwise.

To aid understanding, in the context of the present application the underlying measurement method is first explained with reference to FIGS. 3 to 8, as in the older patent application DE 10 2013 226 887, the disclosure of which is hereby expressly incorporated by reference into the subject matter of the present application. Here, the disclosure is explained below by way of the example of an inductive proximity sensor, even though the method can also be used for any other principles of measurement as desired, such as in particular capacitive or resistive measuring systems, or indeed optical and chemical measuring systems, provided the physical measured value is converted to an electrical value. Thus, in FIG. 3 all that would be needed would be to replace the transmitting/receiving coil system 1.1 by a sensor unit that operates correspondingly differently.

Figure 3:
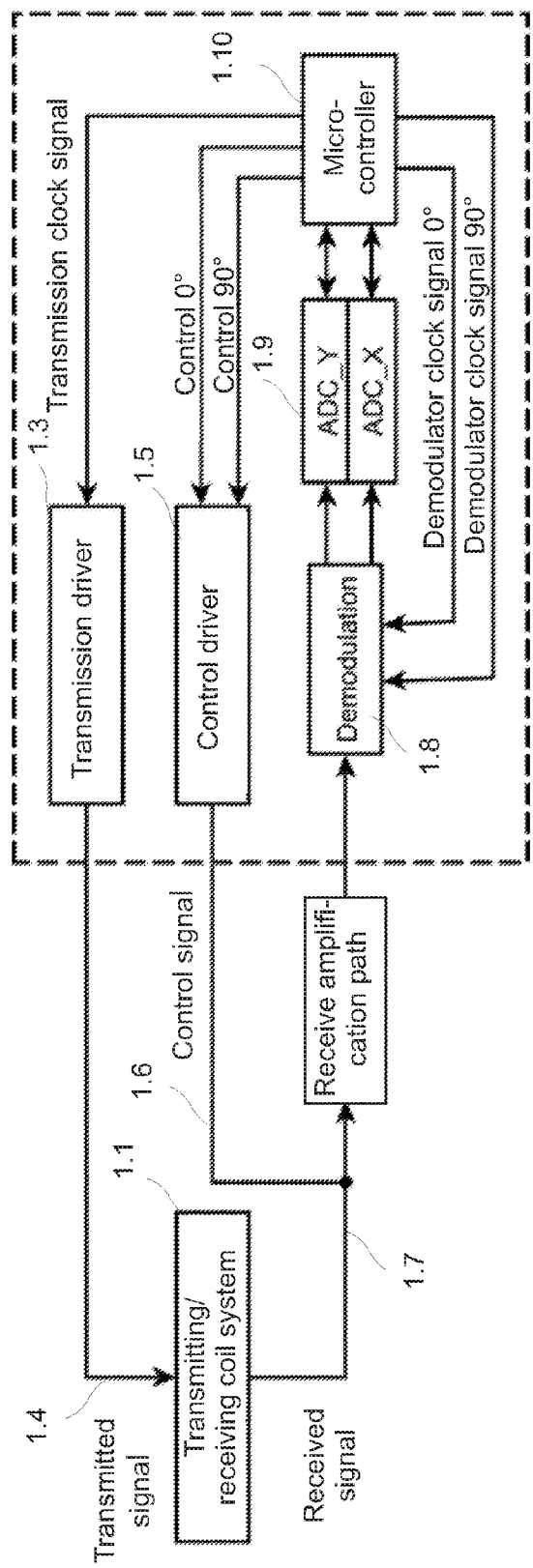
FIG. 3 shows a schematic block circuit diagram of the system components according to the older patent application DE 10 2013 226 887.
Figure 5:
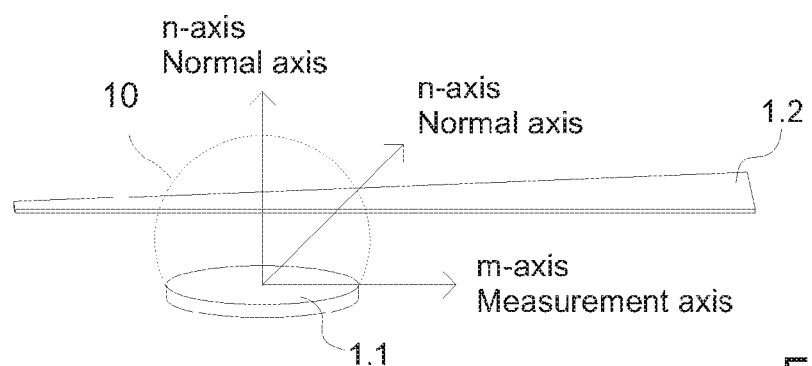
FIG. 5 shows a three-dimensional side view of a target with an associated transmitting/receiving coil system as the sensor unit.
Figure 6A:
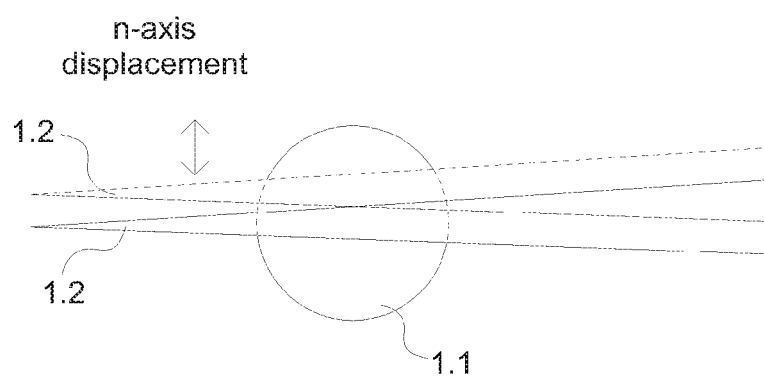
FIGS. 6a, 6b show a plan view of the illustration according to FIG. 5, with the target displaced along the n axis and with the target displaced along the measurement axis m.
Figure 6B:
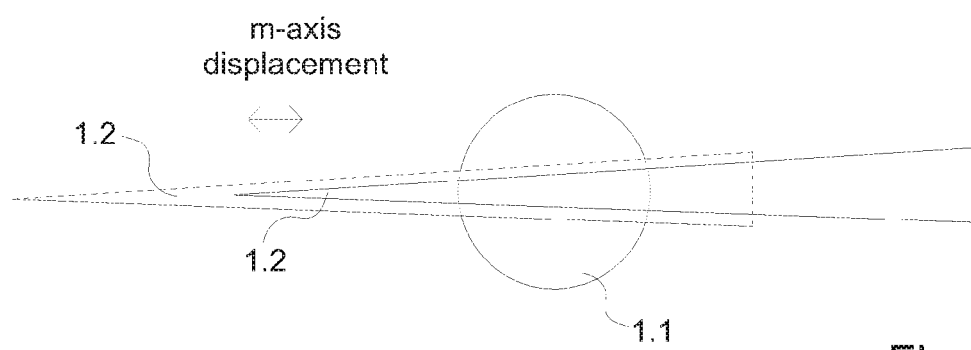

In an inductive proximity sensor, for the purpose of determining at least one physical parameter of at least one target 1.2—for example the position or the type of material of the target is detected—which is illustrated in FIGS. 5 to 6b, at least one transmitting/receiving coil system 1.1 is provided as the sensor unit, according to FIG. 3. The transmitting/receiving coil system 1.1 creates a detection region 10 according to FIG. 5. A transmission driver 1.3 delivers a periodic excitation 1.4, at a transmission frequency of for example 200 kHz, to the transmitting coil of the transmitting/receiving coil system 1.1. The excitation signal delivered to the transmitting/receiving coil system may for example be a square or sinusoidal signal. The transmitting/receiving coil system is of a geometric shape and/or is calibrated such that when there is no target in the detection region 10 the received signal that is emitted by the excitation 1.4 is zero or approximating to zero. In the exemplary embodiment of FIG. 3, a target in the detection region 10 brings about an inductive effect and hence a signal not equal to zero in the receive path as the output signal 1.7 of the transmitting/receiving coil system 1.1, this signal having a particular amplitude and phase.

The construction of the transmitting and receiving coil may in principle be for example as in German patent application DE 10 2012 001 202 A1. Here, the normally circular windings of a coil are substantially configured in a meandering shape. Therein the transmitting coil is offset slightly from the receiving coil at a rotational angle.

As regards the amplitude and phase, and as regards the concrete construction of the transmitting/receiving coil system with transmitting coil and receiving coil, the reader is referred to the explanation in WO 2012/104086 A1, although that operates using an analogue closed-loop control. To summarize, that document makes it clear that the excitation 1.4 has a periodic clock frequency as a result of the transmission clock signal, with the result that a target 1.2 in the detection region 10 brings about an amplitude and phase that results in an output or received signal. This signal is transferred, after an appropriate evaluation, to be described below, to the microcontroller 1.10, which drives the control driver 1.5 in a closed-loop control circuit such that a control signal 1.6 is delivered to the receive path such that the signal in the receive path is compensated and becomes zero or approximating to zero. The signal in the receive path may be amplified by means of the amplifier 13.4 to almost any desired extent before demodulation, since in principle only the deviation from the compensated condition is present in the signal. Signal preparation and the interpretation of the measured values, and control, are implemented by the microcontroller 1.10.

By means of its control signal 1.6, the control driver 1.5 always ensures that a signal not equal to zero which is triggered in the receive path, for example by a target 1.2, is compensated to zero. The control signal accordingly exactly replicates the electromagnetic effect of the target 1.2 on the transmitting/receiving coil system. Here, a deviation $\Delta x$, $\Delta y$ from the compensated condition, as an item of information for inductive detection of the target, is inherent in the control signal 1.6. This item of information can then be evaluated accordingly.

According to FIGS. 5, 6a, 6b, for this purpose there is used as the measurement variable that acts on the inductive signature—that is to say acting thereon in the manner in which for example the deviations $\Delta x$ and $\Delta y$ appear in a four-quadrant presentation—a shape of target 1.2 that varies in a direction of measurement m. FIGS. 5, 6a, 6b relate to a target 1.2 that tapers in or in opposition to a particular direction of measurement m. Instead of the tapering of the target, other shapes and inhomogeneous compositions or material combinations that have an effect on the inductive signature are also conceivable. For example, the target may also change its shape in steps in the direction of measurement m. It is also conceivable for the composition of the target 1.2 to change in the direction of measurement m, because for example an inhomogeneous composition is used. Conductor tracks and/or oscillating circuits may also be used as the target. The only important criterion is that the transmitting/receiving coil system 1.1, as the sensor unit, has a detection region 10 and is connected such that in the absence of the influence of metal in the detection region at the output of the transmitting/receiving coil system 1.1 the output signal is a zero signal. If there is a target 1.2 in the detection region 10, the output signal is a signal that is not equal to zero and has a particular amplitude and phase.

The deviations $\Delta x$, $\Delta y$ of the control signal are applied to an x, y coordinate system in a four-quadrant presentation, wherein the origin 2.7 of the x, y coordinate system corresponds to the compensated condition of the transmitting/receiving coil system 1.1 in which the control signals are zero or are calibrated to zero. In this four-quadrant presentation of the deviation $\Delta x$ and the deviation $\Delta y$ of the control signal, the angle that an imaginary vector 2.6 that leads from the origin 2.7 to a measurement point 2.5 makes with the x axis of the x, y coordinate system is a measure of the movement of the target 1.2 in the direction of measurement m. The magnitude of the imaginary vector 2.6 is a measure of the distance of the target 1.2 normal to the direction of measurement m. The significant point here is that the control values and not the detected output signals, such as the signal that is not equal to zero, of the sensor unit are used for the evaluation in the context of the four-quadrant presentation.

In this exemplary embodiment, in the context of a motion sensor the position or situation of a particular target whereof the shape and/or composition are known is determined by determining the position of the target on the m axis and the distance from the m axis, for example according to FIG. 5. However, the sensor unit may also be utilized to operate as a proximity sensor, that is to say there is no known target but rather an object is located in or moves for example into the detection region 10 of the sensor. In this case, the magnitude of the imaginary vector is a measure of the distance of the object from the sensor unit and the angle that the imaginary vector 2.6 makes with the x axis of the x, y coordinate system is a signature of the material, that is to say the characteristic of the material is mirrored in this signature, such that for example the size and/or nature or material of the object can be determined therefrom. One area of use is for example also the identification of rust on iron in a material that is not accessible from outside, for example reinforcing steel inside concrete.

In the case of a capacitive embodiment, changes in the electrical field in the presence of a known target but also in the presence or movement of an object in the detection region also result in changes in the control values which may be evaluated in a manner analogous to that described above in the context of vector analysis. One area of use for capacitive measurement is for example the identification of moisture inside concrete or a screed.

However, the procedure is also similar in the case of other measurement methods. Provided the control values for compensating changes in the detection region have been applied, and not the output signals of the sensor unit in a four-quadrant presentation, these control values result in characteristic signatures for these changes, and positional information that allows object identification and differentiation.

The method sequence is explained with reference to the flow diagram according to FIG. 4. Once the system has been started, in step 100, first a calibration is performed, and where appropriate compensation is performed, according to step 101. For this, the values of the analogue-to-digital converter 1.9 are input in step 102. Depending on the measured values, a check is performed in step 103 as to whether compensation is required. Hence, the microcontroller 1.10 specifies values for the control driver 1.5 in step 104 in order to compensate for any tolerances in the system. This procedure is carried out for both phases of the transmission clock signal until the values of the A/D conversion reach a predetermined value, for example the center of the dynamic range of the A/D converter. Typically, this procedure lasts only a few milliseconds. Thereafter, the tolerances of the coil system and any environmental influences are compensated. If the result in step 105 is then that calibration is required, the measured values of the A/D conversion are stored in step 106 and from then on serve as the calibrated zero point of the system.

Now the actual measurement begins, that is to say that the effect of the target 1.2 on the inductive system is measured. This effect gives the deviation Δx and Δy from the calibrated zero point, according to step 108. From these deviations it is possible to determine the inductive signature, that is to say a measure of the inductive effect of the target 1.2 in the direction of measurement m, according to step 109, and a measure of the distance of the target 1.2 from the compensated condition normal to the direction of measurement m, according to step 110. These values can be cross-referenced in a table of values according to step 111, in order for example to identify the composition of the material. However, they may also serve to determine the position, shape and distance of the target 1.2 in the directions of measurement. The values determined in this way can be displayed according to step 112. When there is no known target, as an alternative the approach of an object and its signature may also be determined as indicated above, regardless of the measurement method. The method runs continuously, that is to say that after step 112 the system jumps back to step 102. This continuous control preferably ends only when the system is taken out of service.

Returning to FIG. 5, a structure having a wedge-shaped, tapering target and a transmitting/receiving coil system 1.1 is shown. The coordinate system m, n, n is applied in this application such that, taking the transmitting/receiving coil system 1.1 as a starting point, the m axis defines a change in position in this system on a measurement axis, while a change in position on one of the n axes is a change in the position of a target extending normal to this measurement axis. A movement along one of the n axes thus changes the distance of the target 1.2 from the transmitting/receiving coil system. The two n axes are hence normal to the m axis. FIG. 5 shows a three-dimensional side view of a system of this kind; FIGS. 6a, 6b show a plan view. A movement of the target 1.2 into the area illustrated in dashed lines in FIG. 6a is thus a movement along the n axis, and shows for example a displacement relative to the transmitting/receiving coil system 1.1, transversely in relation to the m axis. By contrast, a movement according to FIG. 6b is a movement in the direction of the m axis, which is preferably the direction of measurement.

The target 1.2 is illustrated only schematically in the Figures. Within certain limits, for measurements in the direction of measurement, the m axis, the measuring system is independent of tolerances relating to the n axis.

Figure 7:
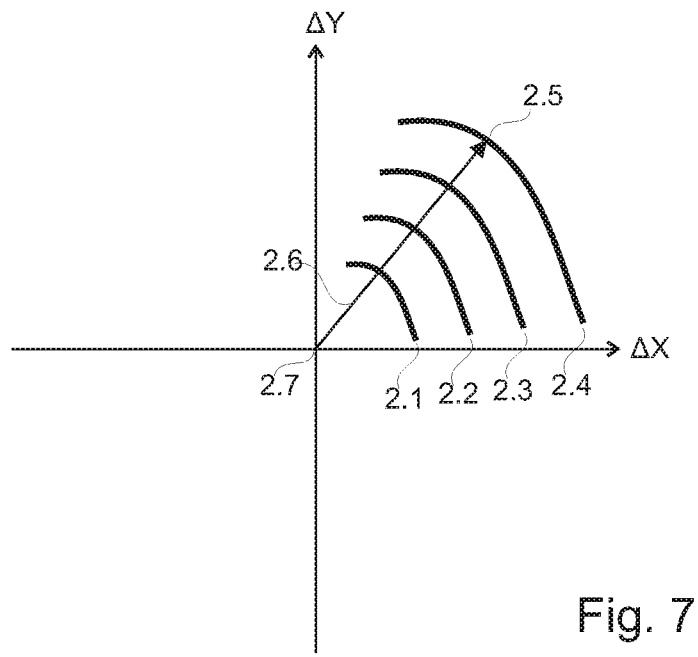
FIGS. 7, 8 show a four-quadrant presentation of the deviations of the control signals.
Figure 8:
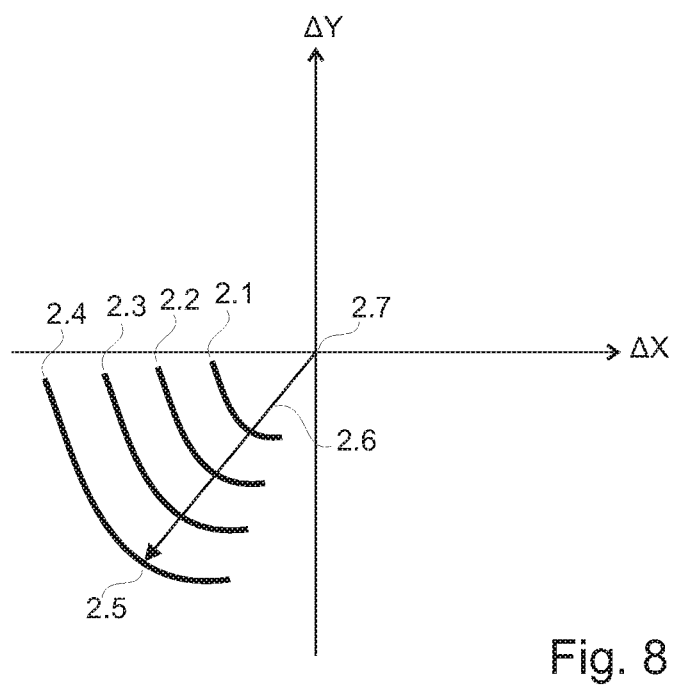

FIGS. 7 and 8 show the signals applied to a four-quadrant presentation. The measured value curves 2.1 to 2.4 result from passing a wedge-shaped target through the detection region 10, along the m axis, with four different distances from the m axis. It can be seen that as the distance becomes smaller, the curve of the position from measured value curve 2.1 to measured value curve 2.4 moves away from the origin 2.7. The curve 2.1 thus shows the signal profile with a large distance from the target to the sensor, and the curve 2.4 shows the signal profile with a small distance from the target to the sensor. At the same time, it can be seen that the curves are scaled. If the target 1.2 is displaced in the direction of measurement m without a displacement in a direction normal to the direction of measurement m, such as in the direction of the n axis, the direction of an imaginary vector 2.6, or the angle between the x axis and an imaginary vector 2.6 from the origin 2.7 to the measurement point 2.5, changes. Thus, the direction of the vector exclusively represents a measure of the movement of the target 1.2 in the direction of measurement m. In practice, this means for example that a target having a length of approximately 50 mm and a tapering from 7 mm to 2 mm brings about a change in the angle that the vector makes with the x axis from 21.5° to 46.2°.

If there is a movement normal to the direction of measurement m, and hence in the n direction, without a displacement along the m axis, the magnitude of the imaginary vector 2.6 from the origin 2.7 to the measurement point 2.5 changes. The magnitude of the vector describes the distance of the target from the coil system. The direction of the vector, which describes the inductive signature, remains the same, however. Thus, the magnitude of the vector represents exclusively the position of the target, that is to say the distance from the target to the coil system.

The signal profile shown in FIG. 7 is only exemplary. In the case of targets of different materials or shapes, signals may also be produced in other quadrants or with different target-specific signal profiles. Thus, for example, FIG. 8 shows application to the third quadrant.

Figure 4:
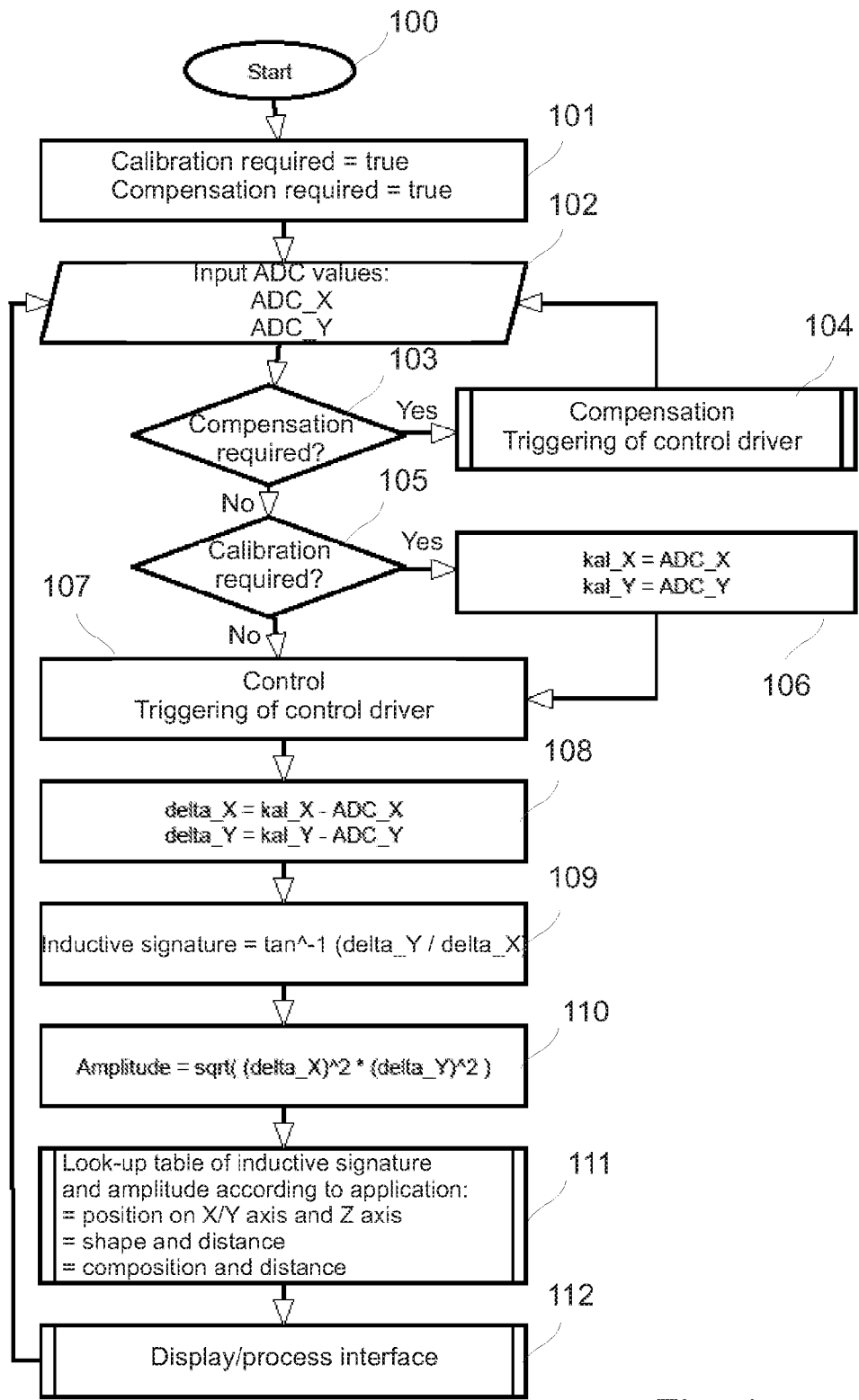
FIG. 4 shows a flow diagram of the procedure when evaluating the measured value using a sensor unit according to FIG. 3.

In order to identify from these illustrations the position and distance of the target 1.2 in relation to the coil system, the deviations Δx, Δy of the control signal that are determined according to FIG. 4 are interpreted such that in step 108 the magnitude of the vector $B_v$ is produced from the root mean square of the deviations from the calibrated zero point, that is to say:

$$B_v = \sqrt{\Delta X^2 + \Delta Y^2} \qquad \text{Formula 1}$$

This magnitude of the value corresponds to the distance of the target 1.2 from the coil system. The position of the target on the m axis is produced from the direction of the imaginary vector 2.6:

$$S_i = \tan^{-1}\left(\frac{\Delta Y}{\Delta X}\right) \qquad \text{Formula 2}$$

$S_i$ represents the inductive signature and corresponds to the position on the m axis. The values $B_v$ and $s_i$ may be used as numerical values in further applications. Using special algorithms that are generated for the corresponding application, or a table of values generated therefor in which standard values of amplitude and inductive signature are stored, different measurement variables may be inferred according to step 111, depending on the application. Possible measurement variables when a target is used are for example:

the position of a target on the m axis, and the distance from the m axis the composition and distance of a target the shape and distance of a target The first measurement variable ($S_i$) is determined by the direction of the imaginary vector 2.6, or its angle with the x axis, and the second measurement variable ($B_v$) is determined by the magnitude of this vector.

When there is no target, and in the presence and/or in the case of movement of an object in the detection range—regardless of the physical parameter concerned—the direction of the imaginary vector 2.6 or its angle with the x axis result in a measurement variable for the signature of the object, that is in particular the size and characteristic or nature of the material of the object, whereas the distance from the sensor unit is determinable from the magnitude of this vector.

Figure 2:
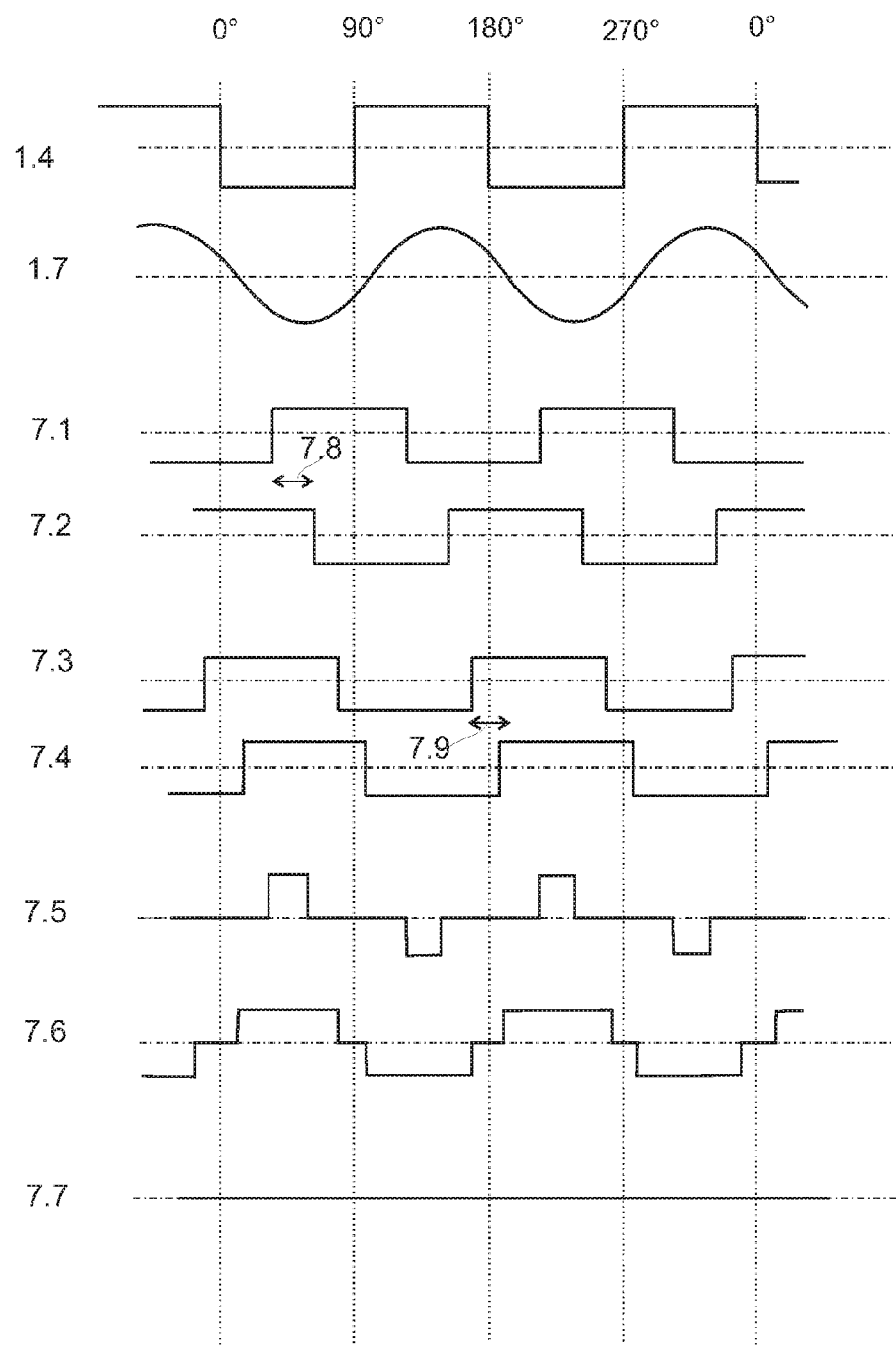
FIG. 2 shows signal profiles in the course of controlling the received signal from the sensor unit to give zero.

FIG. 2 shows the signal profiles when determining a correction signal for compensating an output signal 1.7 of the sensor unit that is generated by the excitation 1.4 in the transmitting/receiving coil system 1.1 and is influenced by the presence of a target 1.2. This output signal 1.7 is reduced, for example by filters, substantially to the fundamental wave of the excitation 1.4. By means of at least one pulse width modulation, a respective correction signal 7.5, 7.6 of variable pulse width and where appropriate variable phase is generated and summed with the output signal 1.7 of the transmitting/receiving coil system 1.1, and in this way the output signal in the entire phase space is controlled to zero or approximating to zero.

Figure 1:
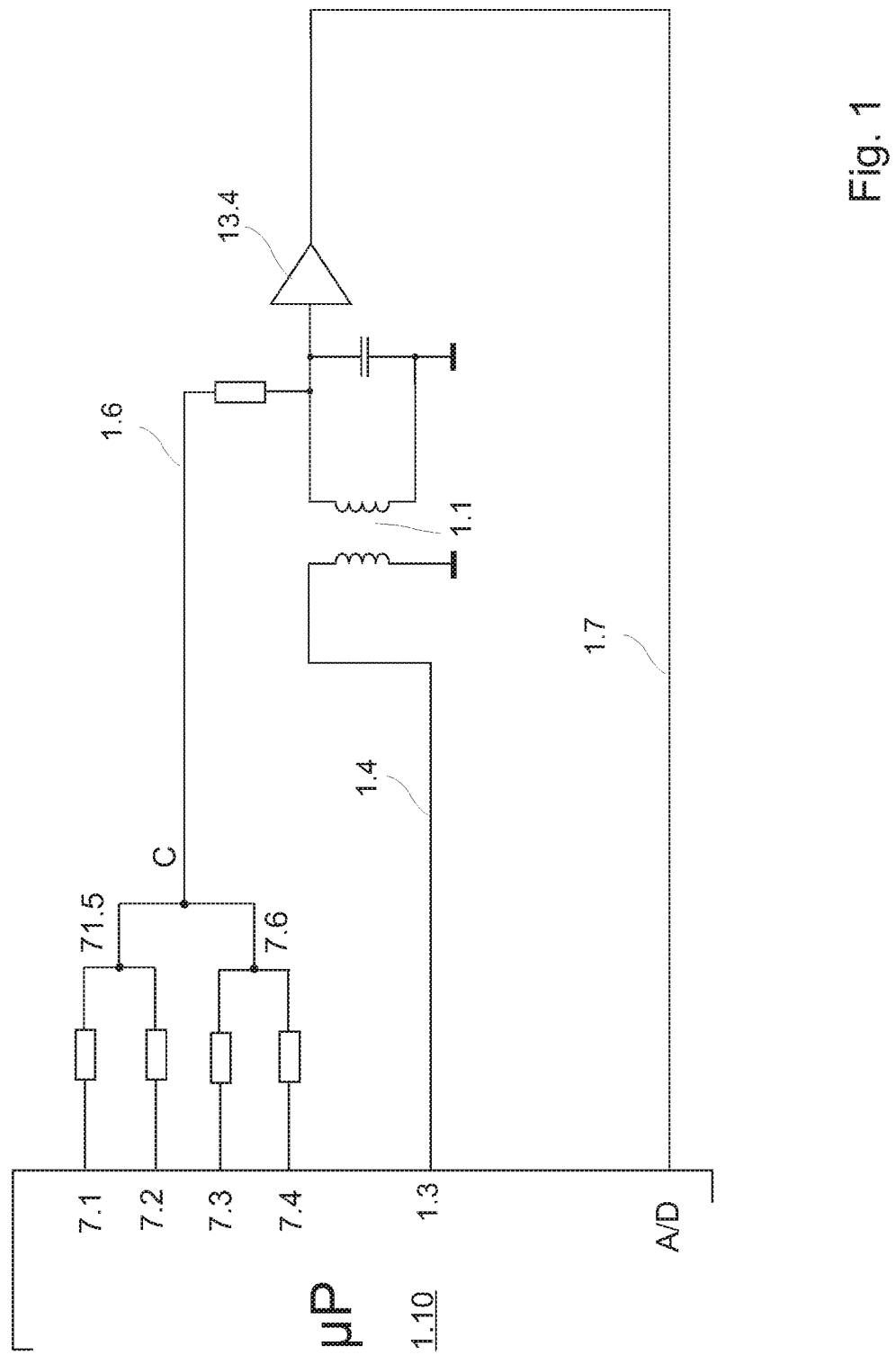
FIG. 1 shows a schematic illustration relating to signal processing.

The method may be operated with only one pulse width modulation, in which the pulse width and the point in time are variable. Preferably, however, a plurality of pulse width modulations is provided that generate correction signal components as individual signals whereof the sum forms the correction signal, wherein each pulse width modulation determines the pulse width of the correction signal symmetrically about a phase point, that is to say the individual signal extends from a determined point in both directions in time and is not extended in length from a point in only one direction in time. The pulse width modulation is thus itself used as a signal, wherein, with a plurality of pulse width modulations, the individual signals, displaced in relation to one another, give the actual pulse width modulation by being summed with one another outside the microprocessor 8 that generates the pulse width and where appropriate the phase of the individual correction signal component. In FIG. 2, the signal profiles 7.1, 7.2 represent a first pulse width modulation, the pulse width being influenced by the fact that the pulses are displaced in relation to one another according to the arrow 7.8. The signal profiles 7.3, 7.4 form a further pulse width modulation in which the pulse width is influenced by the fact that the pulses are displaced in relation to one another according to the arrow 7.9. By summing the signal profiles 7.1 and 7.2 and the signal profiles 7.3 and 7.4 respectively, as also illustrated in FIG. 1 the correction signals 7.5 and 7.6 are produced, which are summed to give the summed signal C, which compensates the output signal of the sensor unit to give the signal profile 7.7.

FIG. 2 shows that the correction signals 7.5 and 7.6, or rather correction signal components, are generated as a tri-state signal. The correction signals 7.5 and 7.6 and their combination to give the summed signal C generate a multi-state signal. The correction signal components are generated at 0° and 180° and/or at 90° and 270°, in each case inverted. With a plurality of pulse width modulations, as illustrated in FIGS. 7, 8, the pulse widths at the phase points 0° and 180° are determined independently of the phase points at 90° and 270°. Moreover, the phase points at 0°, 90°, 180° and 270° may be selected independently of the phase of the excitation signal 1.4.

To implement the method, the output signal 1.7 is scanned, at least two scanning time points in the phase space that are offset from one another by 90°. Preferably, the correction signal is formed by at least a first and a second coefficient of a Fourier analysis.

The input of a correction signal at a particular point in time brings about the maximum change in the output signal 1.7 at another point in time. In order to achieve the optimum effect from the correction signal, scanning is performed, for control of this correction signal, at the particular point in time that is associable with the maximum change. Typically, there is thus a time offset between the summed signal C that is reached by summing the correction signals 7.5 and 7.6, as the control signal 1.6, and the output signal 1.7.

If at least four scanning time points are provided, as in FIG. 2, the values of two scanning time points that are offset by 180° are controlled in relation to one another to give a difference of zero.

In order to eliminate the influence of temperature on the electronic components, the signal not equal to zero in the receive path is compensated to zero directly at the location at which it is produced, that is to say at the sensor unit or, in this case, at the transmitting/receiving coil system 1.1.

The values of correction signal components with no target are used as a zero point for measurement or as a zero point for vector analysis, as described in the introduction. This means that at least one deviation Δx, Δy of the control signal from the compensated condition is inherent in the control signal 1.6, as an item of information on the inductive effect such as the type and/or position of the target 1.2 in relation to the transmitting/receiving coil system (1.1).

FIG. 1 shows the control loop of the system operated according to the method. The control signal 1.6 is determined in that, in a digital evaluation, the signals 7.1, 7.2 of a first pulse width modulation that are determined at 0° and 180° are summed to give the correction signal 7.5. The signals 7.3 and 7.4 of a second pulse width modulation that are determined at 90° and 270° are summed to give the correction signal 7.6. The sum of the correction signals 7.5 and 7.6 results in the summed signal C, which acts on the system directly at the sensor unit, that is to say in this case the transmitting/receiving coil system 1.1. If deviations in the output signal occur in the coil system, for example as a result of approaching metal, they are amplified by way of the amplifier 13.4, supplied to the microprocessor 8 as the output signal 1.7 and then compensated again by way of the pulse width modulation.

The summing resistors may be part of the voltage divider, in order to divide the signal supplied to the receiving coil down to correspondingly small values. In practice, however, a single high-value resistor, for example of 330 kΩ, directly at the sensor unit as the receiving coil, has proved advantageous, in which case the summing resistors then have a value of for example 10 kΩ. Any other type of voltage division may be used to reduce the energy that is introduced.

Abstracting this to any desired sensor unit, therefore, at least one physical parameter is determined by means of a sensor unit that is excited by at least one periodic excitation 1.4. The sensor unit has at least one detection region 10 in which changes in the parameter in the environment around the sensor unit result in an output signal 1.7 from the sensor unit. The sensor unit is connected such that, if there are no changes in the parameter in the detection region 10, the output signal 1.7 at the output of the sensor unit is a zero signal or a signal approximating to zero, whereas in the event of changes in the parameter in the detection region 10 the output signal 1.7 is a signal not equal to zero and having a particular amplitude and phase. In a closed-loop control circuit, the signal not equal to zero is compensated to give a zero value by a control signal 1.6 in the receive path, even if there are changes in the parameter in the detection region 10, for the purpose of achieving a compensated condition. The output signal 1.7 of the sensor unit is reduced substantially to the fundamental wave of the excitation 1.4. At least one pulse width modulation generates in each case a correction signal of variable pulse width and where appropriate variable phase, and sums it with the output signal 1.7 of the sensor unit, and hence controls the output signal to give zero in the entire phase space. The pulse width of the correction signal and/or the phase of the correction signal is determined by the deviations of the output signal 1.7 from zero.

It is self-evident that this description may be subject to the broadest possible variety of modifications, changes and adaptations which are within the range of equivalents to the attached claims.

The invention claimed is:

1. A method for determining at least one physical parameter by means of a sensor unit that is excited by at least one periodic excitation, wherein the sensor unit has at least one detection region in which changes in the parameter in the environment around the sensor unit result in an output signal from the sensor unit at an output of the sensor unit,
   wherein the sensor unit is connected such that, if there are no changes in the at least one physical parameter in the at least one detection region, the output signal is a zero signal or a signal approximating to zero, whereas in the event of changes in the at least one physical parameter in the detection region the output signal is a signal not equal to zero and having a particular amplitude and phase,
   wherein in a closed-loop control circuit, the signal not equal to zero is compensated by a control signal to give a zero value in a receive path of the sensor unit, even if there are changes in the at least one physical parameter in the detection region, for the purpose of achieving a compensated condition,
   wherein the control signal is evaluated to determine the at least one physical parameter,
   wherein the output signal of the sensor unit is reduced substantially to the fundamental wave of the at least one periodic excitation and the output signal is controlled to give zero in an entire phase space by means of at least one pulse width modulation,
   wherein the at least one pulse width modulation itself generates in each case a correction signal of variable pulse width and where appropriate variable phase, and this is summed with the output signal, and controls the output signal to give zero in the entire phase space,
   wherein at least one of the pulse width of the correction signal or the phase of the correction signal is determined by deviations of the output signal from zero.

2. A method according to claim 1, wherein the pulse width modulation determines the pulse width of the correction signal symmetrically about a phase point.

3. A method according to claim 1, wherein a plurality of mutually displaceable pulse width modulations is provided that generate correction signal components as individual signals whereof the sum forms the correction signal, wherein each pulse width modulation determines the pulse width of the correction signal symmetrically about a phase point.

4. A method according to claim 3, wherein the correction signal components are generated at 0° and 180° or at 90° and 270° or at 0° and 180° and at 90° and 270°, in each case inverted.

5. A method according to claim 3, wherein the pulse widths at the phase points 0° and 180° are determined independently of the phase points at 90° and 270°.

6. A method according to claim 1, wherein the output signal is scanned, at at least two scanning time points in a phase space that are offset from one another by 90°.

7. A method according to claim 6, wherein an input of the correction signal at a particular point in time with a detectable time offset brings about a change in the output signal, wherein a point in time at which the change in the output signal reaches a maximum value is further detected, and wherein the scanning time point occurs, for control of this correction signal with the time offset, before the point in time at which the change in the output signal reaches the maximum value.

8. A method according to claim 6, wherein, with at least four scanning time points, values of two scanning time points that are offset by 180° are controlled in relation to one another to give a difference of zero.

9. A method according to claim 3, wherein, with the plurality of pulse width modulations, the individual signals, displaced in relation to one another, give an actual pulse width modulation by being summed with one another outside a microprocessor that generates the pulse width and where appropriate the phase of an individual correction signal component.

10. A method according to claim 1, wherein the signal not equal to zero in the receive path is compensated to zero directly at a sensor head of the sensor unit.

11. A method according to claim 1, characterized in that the correction signal is formed by at least a first coefficient and a second coefficient of a Fourier analysis.

12. A method according to claim 1, wherein values of correction signal components with no target are used as a zero point for a vector analysis.

13. A method according to claim 1, wherein in the event of changes in the at least one physical parameter in the detection region, thus if the output signal is a signal not equal to zero, at least one deviation of the control signal from the compensated condition is inherent in the control signal, as an item of information on the at least one physical parameter.

14. A method according to claim 1, wherein, for the inductive detection of at least one target that has an inductive effect and comprises the at least one physical parameter, as a sensor unit a transmitting/receiving coil system is excited by the at least one periodic excitation,
   wherein the transmitting/receiving coil system has at least two coils and at least one detection region, wherein the transmitting/receiving coil system is connected such that in absence of an influence of metal at an output of the transmitting/receiving coil system the output signal is a zero signal or a signal approximating to zero, while if there is a target in the at least one detection region, the output signal is the signal that is not equal to zero and has the particular amplitude and phase, wherein, in the closed-loop control circuit, the signal not equal to zero is compensated to give the zero value by the control signal in the receive path, even if there are changes in the target in the at least one detection region, for the purpose of achieving the compensated condition, wherein the control signal is evaluated in order to detect the target.

15. A method according to claim 3, wherein the pulse widths at the phase points at 0°, 90°, 180° and 270° are selected independently of a phase of the at least one periodic excitation.

* * * * *